United States Patent
Larocca

(10) Patent No.: US 11,981,930 B2
(45) Date of Patent: May 14, 2024

(54) SUPERCENTENARIAN INDUCED PLURIPOTENT STEM (SCIPS) CELLS AND METHODS OF MAKING AND USING THEREOF

(71) Applicant: Dana Larocca, Alameda, CA (US)

(72) Inventor: Dana Larocca, Alameda, CA (US)

( * ) Notice: Subject to any disclaimer, the term of this patent is extended or adjusted under 35 U.S.C. 154(b) by 566 days.

(21) Appl. No.: 17/110,230

(22) Filed: Dec. 2, 2020

(65) Prior Publication Data
US 2021/0102175 A1 Apr. 8, 2021

Related U.S. Application Data

(63) Continuation of application No. 15/299,927, filed on Oct. 21, 2016, now abandoned, which is a continuation of application No. 13/968,587, filed on Aug. 16, 2013, now abandoned.

(60) Provisional application No. 61/825,053, filed on May 19, 2013, provisional application No. 61/684,047, filed on Aug. 16, 2012.

(51) Int. Cl.
*C12N 5/074* (2010.01)
*G01N 33/50* (2006.01)

(52) U.S. Cl.
CPC ....... *C12N 5/0696* (2013.01); *G01N 33/5044* (2013.01); *G01N 33/5073* (2013.01); *C12N 2506/11* (2013.01); *C12N 2506/1346* (2013.01)

(58) Field of Classification Search
None
See application file for complete search history.

(56) References Cited

U.S. PATENT DOCUMENTS

2014/0056860 A1* 2/2014 Prieur ..................... A61P 21/00
435/377

OTHER PUBLICATIONS

Lapasset et al. (Rejuvenating senescent and centenarian human cells by reprogramming through the pluripotent state, Genes Dev. Nov. 1, 2011; 25(21): 2248-2253).*
Yagi et al. (Establishment of Induced Pluripotent Stem Cells from Centenarians for Neurodegenerative Disease Research, PLoS One. 2012; 7(7): e41572. Published online Jul. 25, 2012).*
Lodi et al. (Stem cells in clinical practice: applications and warnings, J Exp Clin Cancer Res. Jan. 17, 2011;30:9).*
Lewis et al. (Centenarians as stem cell donors, Am J Bioeth. Nov. 2009;9(11):1-3).*
Mahmoudi et al. (Aging and reprogramming: a two-way street, Curr Opin Cell Biol. Dec. 2012;24(6):744-56. doi: 10.1016/j.ceb.2012.10.004. Epub Nov. 9, 2012).*
Rajesh et al., Human lymphoblastoid B-cell lines reprogrammed to EBV-free induced pluripotent stem cells, Blood, Aug. 18, 2011;118(7):1797-800. doi: 10.1182/blood-2011-01-332064. Epub Jun. 27, 2011.*

* cited by examiner

*Primary Examiner* — Aaron A Priest

(57) ABSTRACT

Provided herein are cells and methods for reprogramming iPS cells from a supercentenarian and their differentiated derivatives having differences from non-supercentenarian iPS derived cells that contribute to disease resistance and longevity. Additionally, provided herein are methods for treatment and prevention of age related diseases by administration of therapeutic sciPS derived cells or cell derived reagents. Also provided herein, are methods for identifying reagents for treatment of age related diseases using sciPS cell-based assays.

19 Claims, 2 Drawing Sheets

SUPERCENTENARIAN INDUCED PLURIPOTENT STEM (SCIPS) CELLS AND METHODS OF MAKING AND USING THEREOF

RELATED APPLICATIONS

This application claims the benefit of U.S. Provisional Application No. 61/684,047, filed Aug. 16, 2012; and U.S. Provisional Application No. 61/825,053, filed May 19, 2013, each disclosure of which is hereby incorporated herein by reference in its entirety. In addition, all documents and references cited herein and in the above referenced applications, are hereby incorporated herein by reference.

FIELD OF THE INVENTION

The present invention relates to the field of pluripotent stem cells and cells derived therefrom; such as through reprogramming techniques, that have a genotype associated with extreme human longevity; and their uses for treatment and prevention of age related degenerative diseases and for conferring longevity to non-supercentenarians.

The present invention also relates to the field of techniques for identification, development, and/or generation of developmentally regulated genes, proteins, stem cell antigens, novel stem cell antibodies, cell markers, a bank of novel antibodies against surface markers on stem cells, and/or antibodies for identification and characterization of progenitor cell populations.

BACKGROUND OF THE DISCLOSURE

Extremely long lived humans, supercentenarians, present an excellent model for studying the basis of resistance to degenerative diseases associated with aging. Recent studies on a large cohort aged 90-119 (including 102 supercentenarians) reveal a progressive increase in the age of onset of degenerative diseases with increasing age such that health span begins to approximate lifespan in supercentenarians (Andersen et al. (2012) *J Gerontol A Biol Sci Med Sci* 67: 395). Supercentenarians delay and/or escape degenerative diseases including cancer, cardiovascular disease, dementia, hypertension, stroke, and osteoporosis. Exceptional overall disease resistance among supercentenarians is demonstrated by a progressive compression of morbidity with increased age such that supercentenarians experience only 5.22% years of morbidity compared to 18% among random controls and 9% in centenarians (Andersen et al. supra). Moreover, 70% of supercentenarians escape debilitating disease entirely compared to 30% of 100-104 year olds and 56% of 105-109 year olds (Andersen et al. supra). Taken together these data indicate greater disease resistance in supercentenarians compared to all other groups including centenarians. There is a strong familial component to extreme longevity and recent genome sequence analysis indicates a strong genetic contribution to survival past 100 and this genetic contribution increases with age (Perls et al. (2007) *J Gerontol A Biol Sci Med Sci* 62: 1028) pointing to distinct genetic survival advantages in supercentenarians over other groups including centenarians. Genome Wide Association Studies (CWAS) indicate that longevity is associated with a large number of SNPs (50% in intragenic regions) and have identified genetic signatures among 90% of centenarians that have predictive value for longevity (Sebastiani et al. (2012) *PLoS One* 7: e29848). Surprisingly, the incidence of disease predisposing variants does not decline with exceptional longevity. Taken together these data suggest a strong genetic component to resistance to debilitating disease that contributes to exceptional human longevity (Sebastiani P, Perls T T (2012) *Front Genet* 3: 277). However, the genetic contribution to survival to extreme age is complex, consisting of combinations of many variants which individually have only minor to modest effects (Sebastiani P supra). Therefore, the molecular and cellular basis of the remarkable disease resistance in long-lived individuals is difficult if not impossible to deduce from the genetics alone.

Human pluripotent stem cells, because of their ability to both self-renew indefinitely and to differentiate into virtually any cell type, have the potential to provide an unlimited source of human cells and tissues for research, disease modeling, drug development, and cell replacement therapies. The availability of human pluripotent stem cells is no longer limited to embryonic stem cell sources. Reprogramming technologies for converting somatic cells to induced pluripotent stem OPS) cells by the introduction of defined factors (Takahashi K et al. (2007) *Nat Protoc* 2: 3081) have greatly increased both the number and diversity of human pluripotent cell lines available. Indeed, it may be possible to obtain virtually any human cell type in a rejuvenated state by reprogramming donor cells. Newer reprogramming methods and preclinical studies have addressed initial concerns over the use of early viral based reprogramming vectors (Okano et al, (2013) *Circ Res* 112:523). A rapidly growing application of iPS lines is their use to create cellular models of disease from patient donor cells. For example, Alzheimer's disease, Fanconi's anemia, ALS, and HG progeria are a few of the diseases that have been modeled (Liu et al, (2011) *Nature* 472: 221). Disease modeling with iPS cells can give insight into the cellular and biochemical basis of disease and provide cells for dug screening. However the current paradigm of disease modeling with iPS cells has done little to increase understanding of aging, the greatest risk factor for susceptibility to degenerative diseases. The present invention provides a means of using iPS cells for modeling and recapitulating the cellular basis for resistance to disease that is exhibited by rare extremely long-lived individuals, the supercentenarians.

Prior to the present invention, reprogramming of supercentenarian donor cells has not previously been reported. However, donor cells from individuals up to 109 years of age have been successfully reprogrammed to pluripotency (Yagi et al, (2012) *PLoS One* 7: e4172; Lapasset et al. (2011) *Genes Dev* 25: 2248). In many cases, reprogramming has been found to reset telomeres back to lengths approaching that seen in very young embryonic cells such that the establishment and study of iPS derived cell types with high replicative capacity is possible. However, this has not been previously demonstrated for iPS cells derived from supercentenarians.

Mesenchymal stem/stromal cells (MSCs) play a critical role in the maintenance and repair of many tissues and in providing a niche for hematopoietic stem cells. For example, decreased bone mass seen in age related osteoporosis, a disease that supercentenarians are resistant to, is thought to be at least in part a result of a decrease in osteogenic stem cells (Bergman et al. (1996) *J Bone Miner Res* 11:568; Jilka et al (1996) *J Clin Invest* 97:1732). Indeed, a role for cell autonomous MSC aging and senescence in osteoporosis is indicated by the ability of transplanted of MSCs to delay signs of skeletal aging and confer a survival advantage in a mouse model of accelerated aging (Singh et al. (2013) *Stem Cells* 31: 607). In addition to a loss of proliferative capacity, there are changes in the differentiation propensity from osteogenic to adipogenic that occurs as MSCs age that may account for loss of bone in aging individuals (Moerman et al. (2004) *Aging Cell* 3: 379; Jiang et al. (2008) *J Orthop Res* 26: 910). Transplantation of MSCs from young mice, but not old mice, slows the loss of bone mass in aged mice (Shen et al, (2011) *Sci Rep* 1: 67). Notably, transplantation of MSCs from young donors to aged mice also results in prolonged life span indicating a role for MSCs in overall longevity. Another indication of their repair and maintenance function is that the transfer of MSCs from young mice to aged mice can reverse the effects of aging on maintenance of function in response to cardiac pressure overload (Sopko et al. (2010) *PLoS One* 5: e15187). There is also evidence for a role of bone marrow MSC exhaustion in obesity-induced diabetes (Chen et al. (2009) *Am J Pathol* 17: 701). Thus, MSCs play an important role in the prevention of age related disease and may contribute to determining overall longevity.

Accordingly, a need exists in the art for further investigation and analysis of cellular, molecular, and biochemical properties of stem cells as it relates to their role in disease prevention and longevity. The present invention provides reprogrammed supercentenarian donor derived iPS cells and their differentiated derivatives for identifying factors that impart disease resistance and longevity. In particular, the present invention provides the ability to obtain supercentenarian cells and iPS derivatives with reset telomere length for comparing cellular aging rates in iPS derived cell lines from donors of widely varied ages. Such iPS derived cells are useful as cellular models for understanding how the regulation of cellular aging in supercentenarians contributes to their extreme human longevity and resistance to disease. Additionally, a need exists for elucidating cellular aging through reprogramming of rejuvenated MSCs derived from supercentenarian iPS cells to compare the rate of cellular aging to non-supercentenarian iPS cells. In this regard, differences in proliferative and differentiation capacity with cellular age can be measured and comparative genomic expression analysis used to determine the molecular basis of these differences. MSCs derived from supercentenarians exhibiting cell autonomous differences from non-supercentenarian MSCs in their cellular aging including changes in differentiation capacity would thus be useful for cell replacement therapy and as tools for drug discovery.

In addition, with the number of pluripotent stem cell lines now increasing much more rapidly, it is even more important to develop efficient cell characterization and directed differentiation protocols. Our current knowledge of surface markers that define the various cell types that differentiate from pluripotent stem cells is still limited. Therefore, a need exists for methods relating to the identification of novel developmentally regulated genes, particularly taxonomically restricted genes, and proteins and/or methods relating to the identification, isolation, and differentiation of pluripotent cells and their derivatives.

All documents and references cited herein and in the referenced patent documents, are hereby incorporated herein by reference.

SUMMARY OF THE INVENTION

The present inventor has developed supercentenarian iPS (sciPS) cells, cells derived therefrom; and methods of making and using the sciPS cells and cells derived therefrom. The present invention may be attributed to the fact that extremely long lived humans, supercentenarians, exhibit a remarkable resistance to degenerative diseases associated with aging. As discussed above, data showing a strong familial component to extreme longevity taken with data from the GWAS studies showing a predictive value for longevity, suggest a strong genetic component to resistance to debilitating disease that contributes to exceptional human longevity. However, because the molecular and cellular basis of this remarkable disease resistance is difficult if not impossible to deduce from the genetics alone; the present invention employs reprogramming techniques to elucidate molecular and cellular factors relating to such disease resistance.

Therefore, the present invention utilizes reprogramming for resetting of cellular age by restoring telomere length thus allowing the comparison to be made with both sciPS and control iPS derived cells starting at the equivalent cellular age. Reprogramming donor cells from supercentenarians is used to yield cells that display a disease resistance phenotype that is a consequence of their extreme human longevity genotype. The sciPS derived cells include stem cells for various tissues, for example, neural stem cells, skin stem cells, vascular stem cells, blood stem cells, pancreatic islet stem cells as well as mesenchymal stem cells (MSCs; also known as mesenchymal stromal cells), a cell type that plays an important role in maintaining and repairing multiple human tissues such as bone, cartilage, tendon, and fat, as well as providing a niche for blood stem cells. The sciPS derived cells disclosed herein are used to confer disease resistance and longevity to non-supercentenarians. Comparison of cellular aging of sciPS derived cells such as (MSCs) to control iPS derived MSCs is used to identify intracellular and secreted factors that confer benefits of sciPS derived cells to non-supercentenarian cells. The sciPS derived cells are used in cell-based screens to identify candidate agents that confer sciPS derived cell advantages to non-supercentenarian cells.

Accordingly, disclosed herein is a method of generating stem cells having a reduced rate of cellular aging; the method comprising collecting a cell sample from a validated supercentenarian individual; reprogramming cells from the cell sample into induced pluripotent (iPS) cells; identifying supercentenarian induced pluripotent stem (sciPS) cells which exhibit telomere length resetting; deriving stems cells which exhibit telomere length resetting from the sciPS cells, thereby generating stem cells having a reduced rate of cellular aging as compared to stem cells from iPS cells from a non-supercentenarian donor. In another embodiment, the sciPS cells exhibit full telomere length resetting towards embryonic length. In another embodiment, the supercentenarian individual is a human. In another embodiment, the stem cells are mesenchymal stroma cells (MSC). In another embodiment, the stem cells are hematopoietic stem cells (HSC). In another embodiment, cells from the cell sample are selected from the group consisting of blood cells, dermal fibroblasts, adipose cells, and hair follicle cells.

Also disclosed herein is an isolated population of sciPS cells comprising iPS cells from a supercentenarian individual, wherein the iPS cells exhibit telomere length resetting. In another embodiment, the iPS cells exhibit telomere length resetting towards embryonic length. In another embodiment, the supercentenarian individual is a human.

Also disclosed herein is an isolated population of stem cells derived from sciPS cells; wherein the stem cells exhibit telomere length resetting. In another embodiment, the stem cells exhibit telomere length resetting towards embryonic length. In another embodiment, the sciPS cells are human sciPS cells. In another embodiment, the stem cells are MSCs. In another embodiment, the stem cells are HSCs.

Additionally disclosed herein is a method of cell replacement therapy conferring longevity and resistance to an age-related disease in an individual in need of treatment the method comprising, transplanting stem cells exhibiting telomere length resetting into the individual, wherein the stem cells are from sciPS cells having a reduced rate of cellular aging as compared to non-sciPS cells; and wherein the stem cells confer longevity and resistance to the age-related disease onto the individual; thereby treating the age-related disease in the individual. In another embodiment, the age-related disease is selected from the group consisting of osteoporosis, osteoarthritis, cancer, heart disease, stroke, and neurological disorders. In another embodiment, the individual is a human. In another embodiment, the stem cells are human stem cells. In another embodiment, the stem cells exhibit telomere length resetting towards embryonic length. In another embodiment, the stem cells are MSCs. In another embodiment, the stem cells are HSCs.

Disclosed herein is a method of age-related disease relevant screening of candidate agents; the method comprising contacting the candidate agent with a population of stem cells exhibiting telomere length resetting, wherein the stem cells are from sciPS cells having a reduced rate of cellular aging as compared to non-sciPS cells; and determining the morphologic, genetic, or functional effect of the candidate agent on the stem cells or on cells differentiated therefrom. In another embodiment, the age-related disease is selected from the group consisting of osteoporosis, osteoarthritis, cancer, heart disease, stroke, and neurological disorders. In another embodiment, the stem cells are human stem cells. In another embodiment, the stem cells exhibit full telomere length resetting towards embryonic length. In another embodiment, the stem cells are MSCs. In another embodiment, the stem cells are HSCs. In another embodiment, the candidate agent is selected from the group consisting of biologics, small molecules, drugs, nutraceuticals, cosmeceuticals, compounds, and reagents.

Also disclosed herein is a method of identifying substances capable of tissue homeostasis and immune function regulation; the method comprising culturing sciPS and stem cells therefrom in growth media; and identifying substances in the growth media or in cell extracts. In another embodiment, the sciPS cells and stem cells are human sciPS cells and stem cells. In a further embodiment, the method comprises formulating substances for wound healing. In an even further embodiment, the method comprises formulating substances for regenerative properties of tissues and organs. In an additional embodiment of the method, the tissues and organs are selected from the group consisting of skin, blood, and pancreatic islets.

Additionally disclosed herein is a method of screening candidate agents capable of conferring sciPS benefits to non-sciPS cells; the method comprising contacting the candidate agent with a population of non-sciPS cells; and identifying agents which are capable of conferring sciPS benefits to the non-sciPS cells. In another embodiment, the non-sciPS cells are human. In an additional embodiment, the sciPS benefits conferred to the non-sciPS cells are a reduced rate of cellular aging as compared to non-sciPS cells without the candidate agent. In another embodiment, the candidate agent is selected from the group consisting of biologics, small molecules, drugs, nutraceuticals, cosmeceuticals, compounds, and reagents. In another embodiment, the biologic is a nucleic acid molecule of interest (NOI).

Further disclosed herein is a method for identifying a genetic predisposition to an age-related disease in an individual; the method comprising measuring the rate of decrease in telomere length in a population of sciPS cells to obtain a rate of cellular aging; comparing the rate of cellular aging in the sciPS cells to the rate in non-sciPS cells; calculating a ratio of the cellular aging rate in sciPS cells to non-sciPS cells to obtain predicted genetic lifespan; and determining the predicted disease-free period based on the predicted genetic lifespan and compression of morbidity data from non-supercentenarians, nonagenarians, centenarians, semi-supercentenarians and supercentenarians; thereby identifying a genetic predisposition to an age-related disease in the individual. In another embodiment, the individual is a human. In an additional embodiment, the sciPS cells and non-sciPS cells are human sciPS cells and human non-sciPS cells. In another embodiment, the age-related disease is selected from the group consisting of osteoporosis, osteoarthritis, cancer, heart disease, stroke, and neurological disorders.

The present invention also provides stem cell antigens, stem cell markers, and transmembrane domain containing proteins in stem cells. The present invention also provides techniques for identification of stem cell antigens, markers, and transmembrane domains. The present invention also provides techniques for the identification of ligands that bind to cell surface receptors, and the present invention also provides techniques for identification of the developmental stage and/or differentiation pathway of a pluripotent stem cell. The present invention also provides techniques for the isolation of stem cell antigens, stem cell markers, and transmembrane domain containing proteins in stem cells.

In another embodiment of the present invention, supercentenarian cells, centenarian cells, or cells derived from humans of extreme age are used to produce induced pluripotent stem cell lines. In another embodiment of the present invention, a control cell population is used to identify and isolate distinguishing upregulated or downregulated genes from populations of supercentenarian cells or cloned supercentenarian cells. In another embodiment of the present invention, novel developmentally regulated proteins are identified by probing human embryoid body RNA using oligonucleotide probes that detect expression products of taxonomically restricted genes.

In other embodiments, the methods and cells in the preceding paragraph may additionally incorporate any of the preceding or subsequent disclosed embodiments.

The Summary of the Invention is not intended to define the claims nor is it intended to limit the scope of the invention in any manner.

Other features and advantages of the invention will be apparent from the following Figures, Detailed Description, and the Claims.

BRIEF DESCRIPTION OF THE DRAWINGS

FIG. 1A shows ICC staining of a representative sciPS clone (E19) with OCT4, SOX2, NANOG, Tra-1-60, and Tra-1-81. Figure B shows ICC staining of sciPS-E19 demonstrating differentiation of a representative sciPS clone to ectoderm (Nestin, Pax6), endoderm (Sox17, FoxA2), and mesoderm (Smooth Muscle Actin (SMA)).

DETAILED DESCRIPTION OF THE EMBODIMENTS

Figure 1A:
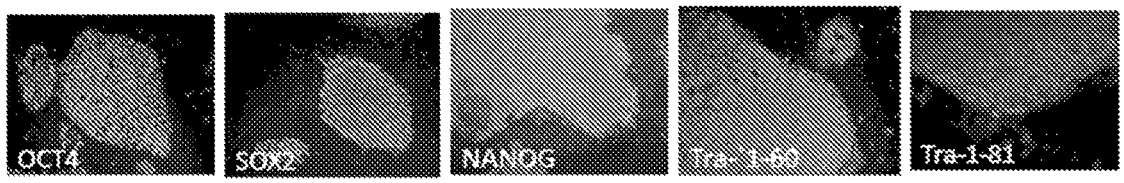
FIGS. 1A and 1B show immunocytochemical (CC) staining of a sciPS derived from a cell line from a 114 year old supercentenarian. Epstein Barr Virus (EBV) immortalized B-lymphoblastoid cells were obtained from a 114 year old female donor with no prior history of cancer, heart disease, blood disorder, lung disease, genito-urinary disorder, gastrointestinal disorder, joint disease, eye disease, neurological or psychiatric disorder, or diabetes. The B-cells were reprogrammed using the integration-free episomal DNA method to introduce reprogramming factors. Six sciPS clones were assessed for pluripotency by detection of pluripotency specific marker genes and differentiation to 3 germ layers. All six clones were positive by ICC staining for 5 pluripotency markers and for differentiation markers of all 3 primary germ layers following culture in appropriate differentiation media.

The present invention is disclosed in the Figures and description. However, while particular embodiments are disclosed in the Figures, there is no intention to limit the present invention to the specific embodiment or embodiments disclosed. Rather, the present invention is intended to cover all modifications, variations, derivatives, and/or equivalents falling within the spirit and scope of the present invention. As such, the Figures are intended to be illustrative but not restrictive.

Unless otherwise defined, all scientific and technical terms used herein have the same meaning as commonly understood by one of ordinary skill in the art to which this technology belongs.

As used herein and in the appended claims, the singular forms "a," "an," and "the" include plural reference unless the context clearly indicates otherwise.

As used herein, the terminology, cell, cell line, and cell culture are used interchangeably and all such designations include progeny and/or derivatives. Thus, the terms pluripotent stem cells and induced pluripotent stem cells include the primary subject cell and cells and/or cell cultures derived therefrom without regard for the number of transfers. It is also understood that all progeny may not be precisely identical in DNA content, due to deliberate or inadvertent mutations. Mutant progeny that have the same function or biological activity as screened for in the originally pluripotent cell or derivative are included. Where distinct designations are intended, it will be clear from the context.

As used herein, the term antibody refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, an isolated nucleic acid molecule or isolated protein or isolated antibody or isolated cell or cells refer to a nucleic acid molecule or protein or antibody or cell that is identified and separated from at least one contaminant nucleic acid, protein or antibody molecule or cell with which it is ordinarily associated in the natural source. An isolated nucleic acid molecule or protein or antibody or cell is other than in the form or setting in which it is found in nature. Isolated nucleic acid molecules therefore are distinguished from the nucleic acid molecule as it exists in natural cells.

As used herein, a nucleic acid molecule or nucleic acid molecule of interest (NOI) means DNA or RNA or a DNA or RNA molecule that is separated from sequences (or nucleotide sequences) with which it is immediately contiguous (in the 5' and 3' directions). For example, the "nucleic acid molecule" may comprise a DNA molecule inserted into a vector, such as a plasmid or virus vector, or integrated into the genomic DNA of a prokaryote or eukaryote. An "isolated nucleic acid molecule" may also comprise a cDNA (complementary DNA) molecule. An isolated nucleic acid molecule manipulated to include other nucleic acid sequences is often referred to as a recombinant molecule. An RNA molecule is composed of nucleotides (ribonucleotides) and is typically single-stranded. RNA is coded by the DNA molecule, or transcribed using the DNA molecule as a template, so that the messenger RNA (mRNA) can be translated into its corresponding amino acid sequence. Short interfering RNA is double-stranded RNA of about 20-25 base pairs (or nucleotides) in length, and which typically function to interfere with the expression of a gene or genes. MicroRNA (miRNA) are very small pieces of RNA which are about 22 nucleotides in length and typically function in the transcriptional or post-transcriptional regulation of a gene or genes. Molecular biology techniques and terminology are readily available and well known and can be found, for example, in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel et al. eds., (2003).

As used herein, pluripotent cells are a population of cells capable of differentiating into all three germ layers and becoming any cell type in the body. Pluripotent cells express a variety of cell surface markers, have a cell morphology characteristic of undifferentiated cells and form teratomas when introduced into an immunocompromised animal, such as a SCID mouse. Teratomas typically contain cells or tissues characteristic of all three germ layers.

As used herein, multipotent cells are more differentiated than pluripotent cells, but are not permanently committed to a specific cell type. Pluripotent cells therefore have a higher potency than multipotent cells.

As used herein, induced pluripotent stem cells or iPS cells are cells that are differentiated, somatic cells reprogrammed to pluripotency. The cells are substantially genetically identical to their respective differentiated somatic cell of origin and display characteristics similar to higher potency cells, such as ES cells. See, Yu J, et al., "Induced pluripotent stem cell lines derived from human somatic cells," Science 318: 1917-1920 (2007), incorporated herein by reference as if set forth in its entirety.

As used herein, an embryoid body or an EB, is an aggregate of cells derived from pluripotent cells, such as ESCs or iPS cells, where cell aggregation can be initiated by hanging drop, by plating upon non-tissue culture treated plates or spinner flasks (i.e., low attachment conditions); any method prevents the cells from adhering to a surface to form typical colony growth. EBs appear as founded collections of cells and contain cell types derived from all three germ layers (i.e., the ectoderm, mesoderm and endoderm). Methods for generating EBs are well-known to one ordinary skill in the art. See, Itskovitz-Eldor J, et al., "Differentiation of human embryonic stem cells into embryoid bodies compromising the three embryonic germ layers," Mol. Med. 6:88-95 (2000); Odorico J, et al., Stem Cells 19:193-204 (2001); and U.S. Pat. No. 6,602,711, each of which is incorporated herein by reference as if set forth in its entirety.

As used herein, taxonomically-restricted gene refers to genomic DNA sequence encoding a peptide or protein sequence that is restricted to a single species distribution (orphan) or to a narrow phylogenetic distribution having homologs in closely related species but not present in more distantly related species or other genera.

The present invention provides iPS cells derived from supercentenarians (sciPS) that are used to create cellular models of decelerated human aging. The sciPS generated cellular models are useful for comparative studies of cellular aging to determine the molecular basis of decelerated human aging.

For purposes of the present invention, a supercentenarian is an individual human having attained an age of at least 10 years from birth; or is an individual non-human animal or mammal having an equivalent age as determined by, e.g., an estimation based on having an age of approximately 90% or greater of the maximal lifespan of the species and/or comparative genomics. Comparative genomics and tools for assessing human equivalence in age in a non-human individual are readily available and well known. (See e.g., Tacutu et al., (2012) Nucleic Acids Research 41: D1027-D1033; Magalhaes et al., (2009) Aging Cell 8: 65-72; Magalhaes et al., (2009) J. Evol. Biol. 22: 1770-74.) Supercentenarian cells or sciPS cells are cells or iPS cells from and/or derived from a supercentenarian.

For the purposes of the present invention, a non-supercentenarian is an individual human from the general population that has attained an age less than 110 years and is not a sibling or parent of a supercentenarian; or is an individual non-human animal or mammal having an equivalent age as determined by, e.g., an estimation based on having an age of less than approximately 90% of the maximal lifespan of the species and/or comparative genomics. Comparative genomics and tools for assessing human equivalence in age in a non-human individual are readily available and well known. (See e.g., Tacutu et al., (2012) Nucleic Acids Research 41: D1027-D1033; Magalhaes et al., (2009) Aging Cell 8: 65-72; Magalhaes et al., (2009) J. Evol. Biol. 22: 1770-74.). Non-supercentenarian cells or non-sciPS cells are cells or iPS cells from and/or derived from a non-supercentenarian.

For purposes of the present invention, a semi-supercentenarian is an individual human having attained an age of 105-109 years from birth; or is an individual non-human animal or mammal having an equivalent age as determined by, e.g., an estimation based on having an age of approximately 86-89% of the maximal lifespan of the species and/or comparative genomics. Comparative genomics and tools for assessing human equivalence in age in a non-human individual are readily available and well known. (See e.g., Tacutu et al., (2012) Nucleic Acids Research 41: D1027-D1033; Magalhaes et al., (2009) Aging Cell 8:65-72; Magalhaes et al., (2009) J. Evol. Biol. 22: 1770-74.) Semi-supercentenarian cells or semi-sciPS cells are cells or iPS cells from and/or derived from a semi-supercentenarian.

For purposes of the present invention, a centenarian is an individual human having attained an age of 100-104 years from birth; or is an individual non-human animal or mammal having an equivalent age as determined by, e.g., an estimation based on having an age of approximately 82-85% of the maximal lifespan of the species and/or comparative genomics. Comparative genomics and tools for assessing human equivalence in age in a non-human individual are readily available and well known. (See e.g., Tacutu et al., (2012) Nucleic Acids Research 41: D1027-D1033; Magalhaes et al, (2009) Aging Cell 8: 65-72; Magalhaes et al., (2009) J Evol. Biol. 22: 1770-74.) Centenarian cells or ciPS cells are cells or iPS cells from and/or derived from a centenarian.

As used herein, induced pluripotent stem (iPS) cells are cells that are derived from a cell sample provided by a donor (e.g. B lymphocytes, EBV transformed B lymphocyte cell line cells, fibroblasts, keratinocytes) using any one of a number of reprogramming methods known in the art that include transcriptional reprogramming (Takahashi K et al. (2007) *Nat Protoc* 2: 3081) and reprogramming by nuclear transfer (Tachibana et al (2013) *Cell* 153: 1). The resulting iPS cells are embryonic stem cell-like in their capacity for self-renewal and differentiation into cell types that are representative of the three primary germ layers of embryonic development (mesoderm, endoderm and ectoderm).

As used herein, telomere length resetting refers to an increase in average telomere length of a cell sample extending from the telomere length at the time the sample is taken from a donor, up to and including restoration of telomere length that approximates telomere lengths of the cell's ancestral cells as they existed in the early embryo.

As used herein, cellular aging refers to changes in a cell that occur with time that impact its capacity to replicate, differentiate, or otherwise function as it would in a young healthy individual before degenerative effects of aging have begun. These changes include shortened telomere length, loss of differentiation capacity, changes in differentiation propensity, changes in genomic methylation pattern (Hannum et al. (2013) *Mol Cell* 49:359), changes in genome expression pattern, morphological changes (e.g. to a large flattened appearance) and expression of senescence associated genes and gene products (e.g. SA-B-galactosidase, senescence associated secretory phenotype). Other changes include accumulation of genomic DNA mutations, mitochondrial DNA mutations, incorrectly folded proteins, intracellular aggregates (e.g. lipofuscin), nuclear abnormalities, and progerin. Additional changes include an increase in sensitivity to stress such as substratum deprivation, serum starvation, electrical stimulation, mechanical stress and hypoxia.

In one embodiment of the invention, sciPS cell derived MSCs are compared to non-sciPS derived MSCs to determine differences in telomere dynamics, telomerase activity, and changes in differentiation capacity with increased replication cycles as measured for example by number of population doublings. The development of sciPS and sciPS derivatives enables comparative transcriptome, proteome and methylome analysis of virtually any cell type in a genetic background of extreme longevity versus normal non-supercentenarian or accelerated aging (e.g. HG progeria, Werner's syndrome). Identified sciPS and sciPS derived cell specific factors are used to design screening assays for compounds that confer sciPS cell benefits to non-supercentenarian cells. The sciPS cells provide a human cell based model system useful for assessing the role of various factors in the aging process such as stress genes (Swindell et al. (2009) *Mech Aging Dev* 130: 393), DNA damage and repair, Surtuins, MTOR, and the insulin-IGF receptor pathways (Barbieri et al. (2003) *J Physiol Endocrinol Metab* 285: e1064). Previously such systems were only available using cells from lower animals such as worms, fruit flies, and mice. The sciPS cells of the present invention are also useful for creating human mouse chimeras to examine human cellular aging in an animal model, such as, in mice with human immune systems derived from sciPS compared to non-sciPS models to identify immune cell factors involved in extreme longevity.

The present invention provides for the derivation and analysis of previously difficult or impossible to obtain supercentenarian tissues such as vascular, heart muscle, neural, liver and pancreas cells with restored telomere length. The rejuvenated sciPS derived cells and tissues allow unprecedented analysis of decelerated human cellular aging. It is impractical to do longitudinal studies on supercentenarians at younger ages. Even if supercentenarians could be identified at young ages, only a few cell types would be accessible (i.e. blood, hair and skin) and these individuals are extremely rare (<1 in 5 million). The sciPS cells provide genetically matched pluripotent cells with rejuvenated cellular age (e.g. restored telomere length). The sciPS cells provide medically relevant cell types from individuals with long-lived genotypes at different replicative ages ranging from embryonic to senescent. The sciPS cells and their derivatives are useful for analyzing function of candidate human longevity genes and single nucleotide polymorphisms (SNPs) associated with extreme human longevity. For example, mutations in RNA editing genes are associated with long lived humans but the functional analysis has been thus far limited to analysis of models based on lower animals such as C. elegans because of a lack of human cells to determine how these mutations which affect RNA editing at the cellular level are involved in aging.

In one embodiment, 4 factor (OSKM) reprogramming using episomal plasmid vectors is used for blood cell reprogramming as previously described (Rajesh et al. (2011) Blood 118: 1797; Choi et al. (2011) Blood 118: 1801; Chou et al. (2011) Cell Res 21:518). EBV-transformed lymphocytes are reprogrammed using the non-integrative plasmid method to introduce the reprogramming factors. Episomal plasmid reprogramming from EBV-transformed B-cells is a known method for successful reprogramming to pluripotent cell lines that are both E8V DNA-free and free of plasmid vector DNA (Rajesh et al. (2011) Blood 118: 1797; Choi et al. (2011) Blood 118: 1801). This approach is advantageous because it provides sufficient cell numbers for reprogramming and because using blood cells avoids risks associated with obtaining fibroblasts using dermal punch biopsy in an aged population. The use of EBV transformed cells has the advantage that a single small blood sample can be taken from which cells are expanded and multiple aliquots are archived for later use.

Also provided herein are methods to obtain rejuvenated sciPS and sciPS derived cells having reset cellular age as well as developmental age to embryonic equivalent. In one embodiment, the telomerase repeat amplification protocol (TRAP) assay is used to measure telomerase activity in sciPS clones. The TRAP assay measures telomerase to identify iPS clones with high telomerase activity. Such clones progressively lengthen telomeres with continued passage until reaching embryonic length of the parental embryonic cell line (Vaziri et al, (2010) Regen Med 5: 345). The sciPS cell clones are monitored for telomere length using standard methods and compared to embryonic stem cell telomere length. The sciPS cell clones are also screened for loss of EBV and episomal plasmid DNA. Pluripotency is assessed by differentiation of the sciPS clones to cell types representative of the three primary (embryonic) germ layers using standard directed differentiation conditions in vitro and by analysis of teratoma formation in mice.

In another embodiment of the present invention, the proliferative capacity, telomerase activity, telomere dynamics, rate of aging with respect to changes in differentiation propensity, and the appearance of senescent cells is determined in sciPS derived stem cells such as MSCs and compared to non-sciPS MSCs. Loss of MSCs with age could lead to stem cell exhaustion which would affect overall health, and for example skin integrity, immune function, and susceptibility to bone fracture because of the role these cells play in maintenance and repair of mesenchymal tissues such as bone, skin, blood and the vascular system. The importance of MSCs is indicated by the prevalence of symptoms related to defects in mesenchymal tissues seen in patients with diseases associated with accelerated cellular aging such as HG Progeria and Werner's syndrome. Proliferative capacity is measured as population doublings from initial derivation through senescence. The rate of change in telomere restriction fragment (TRF) length is measured from DNA extracted from cells with increasing population doublings in culture to measure differences in telomere dynamics between sciPS and non-sciPS derived MSCs. The TRAP assay is used to measure telomerase activity at early and late passages as previously described (Vaziri et al. (2010) Regen Med 5: 345). The percentage of senescent cells is measured by staining for SA-B-galactosidase to assess rate of increase with passage, sciPS derived cells are advantageous over non-sciPS derived cells for maintaining their functional integrity with passage in culture. Early and late passage genomic expression analysis is performed to determine underlying biochemical factors that confer benefits of sciPS derived cell aging.

In another embodiment of the present invention, sciPS derived cells such as MSCs and vascular smooth muscle cells (VSMCs) are assessed for sensitivity to oxidative and mechanical stress and compared to equivalent control-iPS derived cells. There is evidence that premature aging and cardiovascular disease in progeria patients is caused by both a stem cell depletion and increased sensitivity to the low oxygen stress of their niche (Zhang et al. (2011) Cell Stem Cell 8: 31). Depletion of stem cells and increased sensitivity of stem cells to stress is thought to play a significant role in human aging and vascular disease (Zhang et al. Supra Sahin E, Dapino R A (2010) Nature 464: 520). Resistance to stress in sciPS derived cells such as MSCs, VMSC, endothelial progenitor cells (EPCs) is compared to the equivalent non-sciPS derived cells. Early, middle, and late passage cells are subject to hypoxia with and without substrate depletion and VSMCs subjected to mechanical stress as described (Zhang et al. Supra). Cellular aging with respect to changes in stress resistance is measured by percent cell survival and percent of senescent cells in each population with increasing passage number.

In another embodiment of the present invention, specific factors in sciPS derived cells such as MSCs are identified by comparative transcriptomic, proteomics and methylomics. DNA, RNA, and protein samples are analyzed for methylomic, transcriptomic and proteomic changes with increasing cellular age and compared to controls. Loss and gain of functions analysis is used to determine the effect these factors have on sciPS derived MSC cellular aging including changes in differentiation capacity with increased population doubling. The factors are used as indicators in cell based assays to identify compounds including nucleic acids of interest that induce the benefits of sciPS MSCs in non-sciPS derived MSCs.

In another embodiment of the present invention, sciPS derived cells are used to confer supercentenarian benefits such as resistance to degenerative disease, increased health span and longevity (Andersen et al. (2012) J Gerontol A Biol Sci Med Sci 67: 395) to a non-supercentenarian. Bone marrow stem cells including MSCs and HSCs are derived from sciPS using methods known in the art (Liu et al. (2012) PloS One 7:e33225; Suzuki et al. (2013) Mol Ther 21:1424; Klump et al. (2013) Curr Mol Med 13: 815; Bouhassira et al. (2013) Expert Opin Biol Ther 13: 1099). The sciPS derived MSCs and HSCs are used to treat an individual that is at risk for osteoporosis by transplantation of sciPS derived bone marrow stem cells into the at risk individual.

In another embodiment of the present invention, supercentenarian benefits are conferred to a non-supercentenarian by conversion of non-supercentenarian iPS cells from the patient to be treated to cells having sciPS-like properties and deriving cells for cell replacement therapy from the converted patient matched sciPS cells. Conversion of iPS to sciPS-like cells is accomplished by introduction of sciPS factors into iPS using for example established gene therapy methods such as gene editing (Perez-Pinera et al. (2012) Curr Opin Chem Biol 16:268; Li et al, (2013) Mol Ther 21:1259) and gene transfer. The converted iPS cells are used to derive patient matched MSCs with sciPS derived MSC properties. The patient matched MSCs derived from converted iPS cells are used to treat age related degenerative diseases such as osteoporosis by transplantation back to the patient.

In another embodiment of the present invention, supercentenarian benefits are conferred to a non-supercentenarian by treatment with compounds such as small molecules, drugs, nutraceuticals, and nucleic acids that are shown to induce sciPS derived cell properties in non-sciPS derived cells. For example, a compound is used that is shown to induce a reduced rate of cellular aging in non-supercentenarian iPS derived MSCs.

In another embodiment, substances made by sciPS derived cells are used to treat degenerative diseases associated with aging such as damaged skin. Cells derived from sciPS such as MSCs are used to prepare cell extracts and conditioned medium containing sciPS MSC intracellular and secreted substances. The cell extract and/or conditioned medium, or one or more components thereof, which may also be considered a cosmeceutical, is added to dermatological formulations such as creams or lotions and applied to the skin to restore a youthful appearance to age or sun damaged skin by alleviating age related changes in skin such as thinning skin, loose skin, discoloration, hyperpigmentation, fine lines and wrinkles.

In another embodiment of the present invention, the rate of cellular aging of iPS derived cells from a non-supercentenarian is used as a diagnostic assay to assess predicted longevity and the degree of resistance to degenerative disease. A ratio of rate of cellular aging of non-supercentenarian to supercentenarian iPS derived cells indicates longevity and disease resistance on a scale of 0 to 1 with a score of 1 indicating a predicted longevity of at least to age 110 and predicted resistance to degenerative disease equivalent to a supercentenarian. The diagnostic is used to monitor the effectiveness of treatments designed to increase longevity and resistance to age related degenerative disease.

The present invention additionally provides for the isolation of stem cell antigens, stem cell markers, and transmembrane domain containing proteins derived from stem cells. Stein cell antigen proteins may be embodied in many forms, preferably in isolated form. As used herein, an antigen or protein is said to be isolated when physical, mechanical or chemical methods are employed to remove the stem cell antigen or protein from cellular constituents that are normally associated with the antigen or protein. A skilled artisan can readily employ standard purification methods to obtain an isolated stem cell antigen or protein. A purified stem cell protein molecule will be substantially free of other proteins or molecules which impair the binding of the stem cell protein to antibody or other ligand. The nature and degree of isolation and purification will depend on the intended use. Embodiments of the stem cell protein include a purified stem cell protein and a functional, soluble stem cell protein. The present invention also provides techniques for identification of stem cell antigens, markers, and transmembrane domains. The present invention also provides techniques for the identification of ligands that bind to cell surface receptors, and the present invention also provides techniques for identification of the developmental stage and/or differentiation pathway of a pluripotent stem cell. The present invention also provides techniques for the isolation of stem cell antigens, stem cell markers, and transmembrane domain containing proteins in stem cells.

In one embodiment, the present invention provides isolated stem cell DNA, e.g., cDNAs, encoding embryoid body cell surface antigens. In one embodiment of the present invention, the embryoid bodies are human. In another embodiment, the present invention provides methods for isolating human embryoid body cell surface antigens using a signal sequence trap (SST). In an additional embodiment of the present invention, the embryoid bodies are derived from iPS and ES cells.

In one embodiment, present invention provides DNA alone (i.e., without flanking sequences) or as a component of a larger sequence comprising other sequences. For example, a DNA of the invention is suitably provided as a component of an expression cassette or an expression vector. Many examples of expression cassettes, expression vectors and the like are known in the art. Examples of expression vectors for expression in E. coli include pGEMEX, pUC derivatives, pGEX-2T, pET3b and pQE-8. Examples of expression vectors for expression in yeast include pY100 and Ycpad1 Examples of expression vectors for expression in animal cells include pKCR, pEFBOS, cDMS and pCEV4. A suitable expression vector for expression in insect cells is the bacculovirus expression vector pAcSGHisNT-A. Many cell lines and other organisms useful in the expression of proteins are known in the art. Examples of cell lines include the E. coli strains HB101, DH1, x1776, JM101, JM 109, BL21 and SG 13009; the yeast strain Saccharomyces cerevisiae; the animal cell lines L, NIH 3T3, FM3A, CHO, COS, Vero and Hela; and the sf9 insect cell line. Methods for transforming or transfecting cells for the expression of an expression vector are known in the art. The DNA of the invention can also be ligated to a DNA encoding another protein and/or peptide, so that the DNA of the invention is expressed as a component of a fusion protein. Conditions for culturing transformed or transfected cells are also known in the art, as are methods for isolating and purifying the expressed protein and/or fusion protein.

In another embodiment, the invention provides antibodies directed against a protein or fusion protein of the invention. The production of such antibodies may proceed according to known methods using the novel proteins of the invention. Antibodies of the invention may be polyclonal or monoclonal. Production of antibodies may be accomplished by immunizing an animal, such as a rabbit or chicken (for a polyclonal antibody) or a mouse (for a monoclonal antibody), with a protein, fusion protein, or protein fragment of the invention. A polyclonal antibody can be obtained, for example, from the animal serum or egg yolk. To obtain a monoclonal antibody, animal spleen cells may be fused with myeloma cells using standard protocols.

Several signal sequence trap systems have been developed including, but not limited to, those provided in U.S. Pat. No. 6,228,590, which describes a technique for screening for mammalian signal sequences by transforming reporter protein-deficient yeast with nucleic acids comprising mammalian coding sequences fused to a reporter protein and detecting cells that secrete the reporter protein. A similar system using invertase-deficient yeast and an invertase reporter protein is disclosed in EP0907727. Yeast-based signal sequence traps have been used to identify secreted proteins from human DNA (Klein et al., Proc. Natl. Acad. Sci. USA 93:7108(1996); Jacobs et al., Gene 198:289 (1997)), mouse DNA (Gallicioti et al., J. Membrane Biol. 183:175 (2001)), zebrafish DNA (Crosier et al., Dev. Dynamics 222:637 (2001)), *Arabidopsis* DNA (Goo et al., Plant Mol. Biol. 41:415 (1999)), potato DNA (Surpili el al., Anais de Academia Brasileira de Ciencias 74:599 (2002)), and *Candida albicans* DNA (Monteoliva el al., Eukaryotic Cell 1:514 (2002)). Similar trap systems have been developed using mammalian host cells (Gallicioti et al., J. Membrane Biol. 183:175 (2001)) and bacterial host cells (Ferguson et al., Cancer Res. 65:8209 (2000). Reporter proteins that have been used in signal sequence traps include invertase (Klein et al., Proc. Natl. Acad. Sci. USA 93:7108 (1996)), alpha amylase (U.S. Pat. No. 6,228,590), acid phosphatase (PHO5) (Surpili et al., Anais de Academia Brasileira de Ciencias 74:599 (2002)), and beta-lactamase Ferguson et al., Cancer Res. 65:8209 (2000).

In another embodiment of the present invention, cDNAs encoding secreted and membrane bound proteins are selected from day 2-14 EBs. In one embodiment of the present invention, cDNAs encoding secreted and membrane bound proteins are selected from day 2-14 EBs from a library. In another embodiment of the present invention, the library of day 2-14 EBs are of normalized and 5' end enriched EB cDNAs using a SST vector. In one embodiment of the present invention the techniques can be used to identify and select cDNAs from a library constructed from known techniques in the art. In another embodiment of the present invention, the cDNA library is normalized to provide methods for identification and selection of otherwise rare cDNAs. In one embodiment of the present invention, the normalized cDNA library reduces the frequency of the most abundant clones by 10 fold or more while increasing the frequency of the least prevalent cDNAs by two fold or more. Se also Bonaldo, et al., U.S. Pat. No. 5,702,898; Short, et al., 5,763,239; and Short, et al. 6,001,574, each hereby incorporated by reference.

In another embodiment of the present invention, a time course of antigen expression and immunolocalization of target antigens is produced by preparing varyingly differentiated human EBs from iPS and hES cells, differentiation and harvest time points of every hour, every two hours, every three hours, every 6 hours, every 8 hours, every 10 hours, every 12 hours, every 18 hours, every 24 hours, or every 48 hours. In one such embodiment, standard cell culture techniques are used to expand and test IgY antibody binding of the every hour, every two hours, every three hours, every 6 hours, every 8 hours, every 10 hours, every 12 hours, every 18 hours, every 24 hours, or every 48 hour time point cell populations. In one embodiment of the present invention, RT-PCR analysis is conducted by isolating total RNA from 2-, 4-, 6-, 8- and 10-day-old EBs and undifferentiated hESCs using, as a non-limiting example, Tri-Reagent (Sigma, St. Louis, Mo., USA) according to the manufacturer's protocol. In another embodiment of the present invention, EB cDNA is then synthesized from isolated total RNA using any means known to one skilled in the art, including but not limited to MMLV reverse transcriptase RNase H minus (Promega, Madison, Wis., USA). PCR products may then be size-fractionated by electrophoresis on 2% agarose gel.

In another embodiment of the present invention, the antigen identification methods of the invention are used to generate a bank of novel antibodies against surface markers on iPS derived cells for identification and characterization of progenitor cell populations. In another embodiment of the present invention, transmembrane domains and/or alternate reading frame cDNAs are used to select genes encoding surface and secreted proteins in cell populations including, but not limited to, progenitor cells. In another embodiment of the present invention, supercentenarian cells, centenarian cells, or cells derived from humans of extreme age are used to produce induced pluripotent stem cell lines. In one embodiment of the present invention, a control cell population is used to isolate distinguishing upregulated or downregulated genes from populations of supercentenarian cells or cloned supercentenarian cells. In an additional embodiment of the present invention novel developmentally regulated proteins are identified by probing human embryoid body RNA using oligonucleotide probes that detect expression products of taxonomically restricted genes.

The invention will now be described by way of Examples, which are meant to assist one of ordinary skill in the art in carrying out the invention and are not intended in any way to limit the scope of the invention.

EXAMPLES

The following examples are provided to illustrate but not limit the claimed invention.

Example 1: Derivation of iPS Cells from Supercentenarian Donor Cells

Figure 1B:
Figure 2:
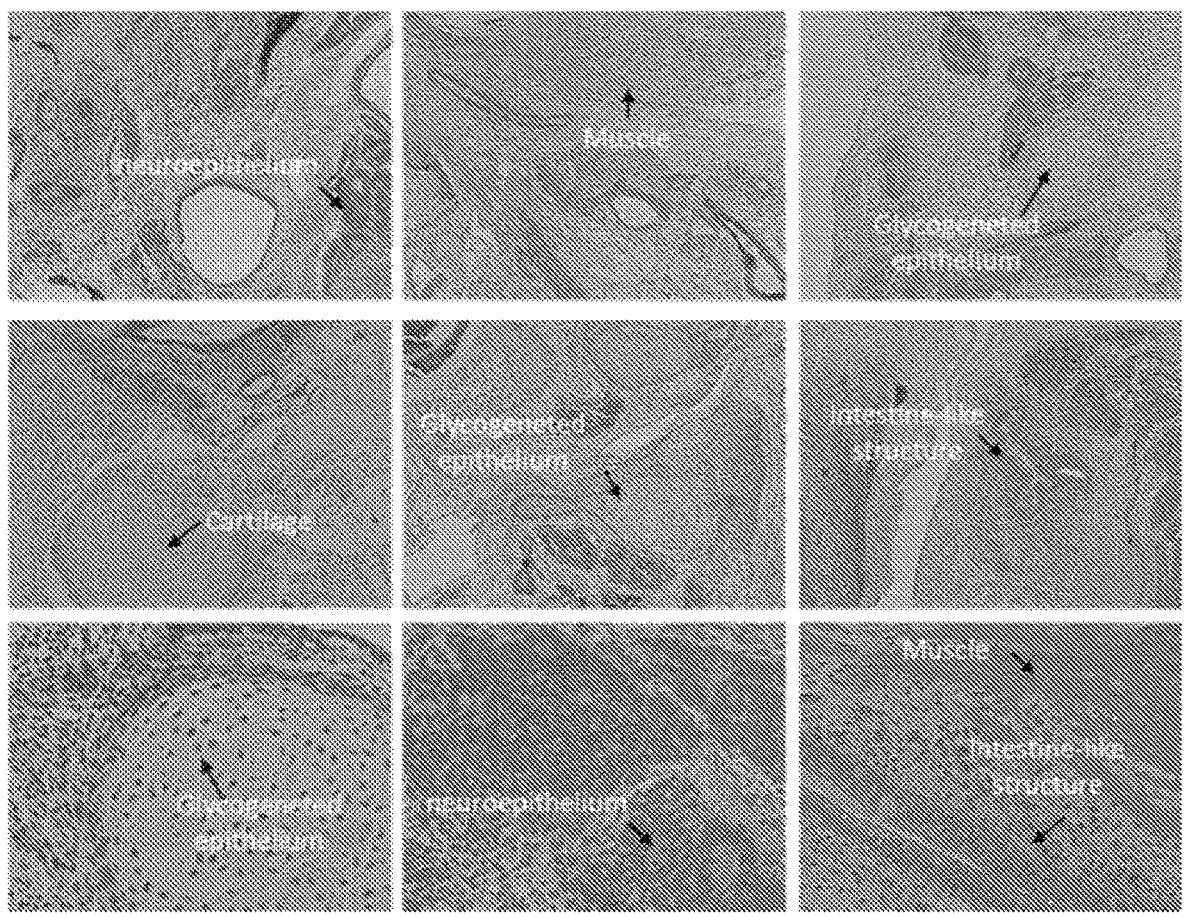
FIG. 2 provides evidence for pluripotency of sciPS-E19 cells by teratoma formation in mice. In vivo differentiation of clonal sciPS-E19 cells to tissues representing ectoderm (neuroepithelium, glycogenated epithelium), mesoderm (cartilage, muscle), and endoderm (intestine) following subcutaneous growth as a teratoma in an immune-deficient mouse (SCID-beige).

The derivation of iPS cells from supercentenarian donor cells is performed by introducing reprogramming factors into the cultured donor cells (Takahashi K et al. (2007) *Nat Protoc* 2: 3081). Methods for reprogramming are well established including the use of viral vectors, episomal plasmid DNA, and RNA to introduce the reprogramming factors or small molecule reagents to activate reprogramming factors. The source of donor cells may be any source known in the art including, without limitation, dermal fibroblasts, hair follicle, and blood. Blood cells (e.g. B-lymphocytes) that have been immortalized by Epstein Barr Virus (EBV) infection are advantageous for obtaining sufficient numbers of cells for reprogramming. Non-viral methods of reprogramming such as integration-free episomal DNA transfection (Okita et al. (2011) *Nat Methods* 8:409) are advantageous because they minimize risk of inadvertent genetic modification that could activate tumor forming ability in iPS cells and their derivatives. Pluripotency of reprogrammed cells is confirmed by immunochemical staining for expression of representative pluripotency markers (e.g. OCT4, SOX2, NANOG, Tra-1-60, Tra-1-80) (FIG. 1A). Pluripotency is also confirmed by demonstrating differentiation to cells of the three primary germ lineages in vitro using standard media formulations and immunochemical staining for representative markers of each lineage (FIG. 1B). Teratoma formation in mice and histological identification of tissue and cell types is used to confirm in vivo differentiation to all three primary germ layers (FIG. 2). Telomerase activity is measured using the TRAP assay (Vaziri et al. (2010) *Regen Med* 5: 345). Telomere length is determined by Southern blot or comparable method. Telomere length in the reprogrammed cells of 12 kb to 20 kb indicates that the reprogramming resulted in a lengthening of the telomeres toward that of embryonic cells. Standard methods such as Southern blotting and polymerase chain reaction DNA amplification are used to confirm loss of episomal reprogramming plasmids and EBV viral DNA (Rajesh et al. (2011) *Blood* 118: 1797; Choi et al. (2011) *Blood* 118: 1801).

Example 2: Derivation of Mesenchymal Progenitor Stem Cells from sciPS and Non-sciPS Cells MSCs are derived from sciPS and non-sciPS cells using previously described methods (Giuliani et al. (2011) *Blood* 118: 3254) such as adherent growth on plastic culture and cytofluorometric sorting of cells positive for one or more MSC markers (e.g. CD105, CD90, CD73, CD44, CD29, CD146, and CD166) and negative for hematopoietic stem cell markers (e.g. CD45, CD34). The isolation of MSCs of clonal purity as described by Lian et al. (Lian et al. (2010) *Circulation* 121:1113) is advantageous for obtaining pure populations of MSCs from iPS cells. Mesenchymal progenitor cells with more limited differentiation capacity (chondrogenic and/or osteogenic) are also obtained using the clonal isolation method described by West et al. (West et al. (2008) *Regen Med* 3:287). The clonal cell line, SM30, described by West, M. D. et al., preferentially differentiates to osteoblasts under osteogenic culture conditions. SM30 cells do not express BMMSC markers (Sternberg et al. (2013) *Regen Med* 8: 125) and unlike BMMSCs, which differentiate to both adipocytes and osteoblasts in osteogenic medium, SM30 cells do not differentiate to adipocytes when cultured in either adipogenic, chondrogenic, or osteogenic differentiation media. Peptides that bind SM30 cell surface are used to identify and purify SM30 cells differentiated from iPS and sciPS cells. Peptides with the sequence DWI-ATWPDAVRS, EWILTLPDGSDW, EWFEFPTPVDA, EWQFWPLLTKN are used to label cells for sorting. The peptides are conjugated to a fluorescent or magnetic tag and peptide bound cells isolated by flow cytometry or magnetic separation. Surface markers are preferentially expressed on SM30 cells in a mixed population of cells that are differentiated from iPS or hES cells using the method described by West et al. (West et al. (2008) *Regen Med* 3: 287). Differential expression analysis of global gene expression data is used to identify genes that are differentially expressed in SM30 relative to other clonal cell lines isolated in parallel under the same differentiation conditions. Upregulated surface markers on SM30 include PTK7, SCARF2, MMP23B, and SEMA3E. Down regulated surface markers include ITGB1 and TNFRSF11B. Advantages of sciPS derived mesenchymal progenitor cell properties relative to non-sciPS derived mesenchymal progenitor cells include reduced rate of telomere shortening and retention of chondrogenic and osteogenic differentiation capacity at later passage number than iPS derived progenitors.

Example 3: Derivation of Clonal Embryonic Progenitor Stem Cell Lines from sciPS The derivation of hundreds of distinct human embryonic progenitor (EP) stem cell lines from human pluripotent stem cells has been previously described (West et al. (2008) *Regen Med* 3:287). These cell lines have been characterized for their global gene expression profile, embryonic origin and lineage differentiation and include cell lines that differentiate, for example to cartilage, bone, smooth muscle, adipose cells and other cell types of interest for research and therapeutic development. The cells have a prolonged but finite replication capacity resulting from extended telomere length typical of embryonic cells. Supercentenarian EP cell lines are similarly derived from sciPS cell lines. The sciPS derived EP cell lines have advantages over non-sciPS derived EP cell lines such as decelerated replicative aging resulting in increased replicative lifespan, increased genome stability and prolonged retention of differentiation capacity compared to non-sciPS derived EP cell lines.

Example 4: Reduced Rate of Cellular Aging and Prolonged Differentiation Capacity of sciPS-MSCs Compared to Non-sciPS-MSCs MSCs are derived from sciPS cells and non-supercentenarian control iPS cells. The rate of cellular aging of sciPS-MSCs is compared to the rate of cellular aging in control non-sciPS-MSCs using known methods. Telomere length shortens with each cell division until reaching a critical length which triggers the cell to enter a non-dividing senescent state. MSC telomere length is monitored using standard assays (e.g. single telomere length analysis (STELA), fluorescence in-situ hybridization (FISH), flow-FISH, and Southern blot analysis). Cells are harvested at passage 0 and at every 5 population doublings until senescence is reached. The telomere length and rate of shortening with population doubling is measured. A reduced rate of cellular aging in sciPS-MSCs compared to control iPS-MSCs is indicated by a slower decrease in the rate of telomere shortening with increasing number of population doublings. A reduced rate of cellular aging is also indicated by elevated telomerase activity as measured using, for example the TRAP (telomere repeat amplification protocol) assay. A reduced rate of cellular aging is also indicated by changes in the epigenetic profile of the cells as described by Hannum (Hannum et al. (2013) *Mol Cell* 49:359). Reduced SIRT1 gene expression is an indicator of cellular aging and therefore retention of SIRT1 expression is an indicator of a reduced rate of cellular aging. There is evidence that the deacetylase encoding gene, SIRT1, gene expression is important for maintaining MSCs with age and for regulating osteogenic capacity (Simic et al, (2013) *EMBO Mol Med* 5: 430). Another indicator of MSC cellular aging is a shift in differentiation potential from one that favors osteogenic differentiation to one that favors adipogenic differentiation. Differentiation potential of iPS MSCs and sciPS-MSC's is measured using standard culture conditions and media that are known to induce osteogenesis or adipogenesis. Differentiation to bone forming cells is measured by assaying deposition of calcium and phosphate in the extracellular matrix using Alizarin Red and Von Kossa staining, respectively. Differentiation to fat cells is measured by staining for intracellular lipid droplets using Oil Red. A reduced rate of cellular aging in sciPS-MSCs is indicated by maintenance of osteogenic differentiation at early middle and late passage whereas non-sciPS-MSCs loose osteogenic differentiation activity at early to middle passage number.

Example 5: Conferred Longevity and Resistance to Age Related Disease

Transplantation of bone marrow mesenchymal stem cells (BMMSCs) from young mice into old mice restores age related bone loss and extends life whereas the equivalent transplantation using BMMSCs from old mice has no effect (Shen et al. (2011) *Sci Rep* 1: 67). Similarly, transplantation of BMMSCs from young mice into a mouse genetically disposed to accelerated aging delays bone aging and confers prolonged survival (Singh et al. (2013) *Stem Cells* 31: 607).

These data support a stem cell autonomous mechanism for tissue homeostasis that results in resistance to age related disease and prolonged survival. Stem cells derived from iPS cells with decelerated aging (sciPS) would be advantageous for transplant because they would provide a longer period of stem cell fitness and therefore a prolonged disease free period and increased longevity. In this example, stem cells derived from reprogrammed supercentenarian pluripotent stem cells (sciPS) are used to confer healthy bone density and an extended period of resistance to osteoporosis than would otherwise be obtained using stem cells derived from iPS cells made from non-supercentenarian individuals. The WRN−/−Terc−/− mouse model is used as a model of age related osteoporosis (Singh et al. (2013) *Stem Cells* 31: 607). Human mesenchymal stem cells (MSCs) from sciPS are prepared (e.g., see Example 2). The cells are supplemented with iPS or sciPS derived HSCs to reconstitute the immune system. Alternatively, the cells are supplemented with whole bone marrow from old (20-24 months) mice. The sciPS-MSCs are transplanted into WRN−/−Terc−/− at 3 months of age (n=10) as described (Singh et al. (2013) *Stem Cells* 31: 607). A second group of mice (n=10) have non-sciPS derived MSCs transplanted and a third group (n=10) serves as untreated controls. The mice are monitored every 3 months for bone density and signs of bone aging (bone volume, cortical thickness, cortical area, total volume, and trabecular number) and survival. A statistically significant number of control iPS-MSC treated mice compared to untreated mice that maintain normal bone density and survive longer indicates the ability of the reprogramming to impart properties comparable to young MSCs. A statistically significant sciPS-MSC treated mice compared to untreated or iPS-MSC treated mice that maintain normal bone density longer and survive longer indicates a slower rate of aging in sciPS-MSCs and their advantage for conferring longevity and resistance to degenerative disease.

Example 6: Identification of Gene Products that Induce sciPS Derived Stem Cell Properties in Non-sciPS Derived Stem Cells MSCs are derived, analyzed and sorted for a panel of MSC surface antigens including CD105, CD73, and CD90 such that only consistent surface marker defined cell populations are used for further analysis. DNA, RNA, and protein samples are analyzed for methylomic, transcriptomic and proteomic changes that occur with increasing replicative age compared to equivalent non-sciPS-MSCs. The data are analyzed to identify differentially expressed genes that distinguish sciPS-MSCs from non-supercentenarian iPS-MSCs. The identified candidate sciPS-MSC genes are tested using inhibitory micro RNAs/siRNAs to knock down gene expression or introduction of the candidate gene using recombinant plasmid DNA or viral gene transfer for over expression. Knocked down genes that result in loss of function (e.g. increase rate of cellular aging, early loss of differentiation capacity) are introduced into non-sciPS in gain of function experiments to determine whether they can induce sciPS-MSC properties in non-sciPS-MSCs. Similarly, genes that when overexpressed in sciPS-MSCs result in loss of function are knocked down in control iPS cells to determine if down regulation induces sciPS-MSC properties in control iPS-MSCs. Micro RNAs or siRNAs corresponding to candidate genes that are down regulated in sciPS are used to identify genes that when down regulated in control iPS-MSCs induce the sciPS-MSC phenotype. The candidate differentially regulated genes are used to determine the effect these factors have on rate of changes in MSC differentiation capacity and other indicators of rate of cellular aging.

In addition, sciPS cells are used in identification of genes useful in surviving degenerative age-related diseases and longevity. Cells are derived from supercentenarian patient(s) from hair follicles or blood or by any other known means. These cells are then reprogrammed using factors according to Yamanaka supra to produce sciPS (induced pluripotent supercentenarian cell) clones. The sciPS clones are assayed for telomerase activity. The clones with high telomerase activity are propagated for 10, 20, 30, or more than 30 passages and telomere length is monitored. The iPSC clones that restore telomere length to 15-20 kb are expanded and banked. sciPS clones are then differentiated spontaneously to embryoid bodies (EB) or in a directed manner to different tissue types including, without limitation, blood, skin, muscle, heart, vascular, liver, lung, and pancreatic islet cells using reagents, and/or cell matrix components and/or cytokines, and/or methods known in the art. Gene expression profiling is then performed on differentiated cells and compared to equivalent cells from known non-supercentenarian controls. Taxonomically restricted (orphan) genes are included in the expression analysis. Alternatively, subtractive cDNA libraries are prepared to enrich for differentially expressed genes that are identified by sequencing. Analysis is performed to determine different upregulation and down regulation of gene products including surface antigens identified as developmentally regulated in the different cell populations and these are tested in animal models (including, without limitation, round worm, fruit fly, and mouse) for their effect on longevity. High throughput drug screening is performed to find agents that induce regulation and/or modulation of gene function that mimics that seen in supercentenarian cells. In vitro aging of the sciPS cells and cells derived therefrom is compared to equivalent cells from a control population to gain an understanding regarding cellular aging processes, and drugs such as, without limitation, biologics, small molecules, drugs, nutraceuticals, cosmeceuticals, compounds, and reagents, are tested in vitro to identify ones that mimic the cellular aging process seen in sciPS cells and cells derived therefrom.

Example 7: Conferred Longevity and Resistance to Disease Using Gene Corrected iPS Derived Stem Cells The genes and gene products identified in Example 6 are tested in vivo for their ability to confer delayed cellular aging and prolonged differentiation of MSCs using gene therapy and gene editing methods to modify expression of endogenous genes in control iPS-MSCs. The gene corrected iPS-MSCs, non-sciPS-MSCs and sciPS-MSCs are compared functionally in a suitable animal model such as the WRN−/−Terc−/− mouse. Successful gene modifications are identified by their ability to confer onto control iPS-MSCs an equivalent bone density and survival advantage as observed with transplantation of sciPS-MSCs.

Example 8: Identification of Compounds that Induce sciPS Derived Stem Cell Properties in Non-Supercentenarian iPS Derived Stem Cells High throughput agent screening on iPS-MSCs is used to identify candidate agents that induce a sciPS-MSC phenotype in iPS-MSCs. Various agent libraries including for example synthetic compounds and natural organic compounds; and siRNAs and cDNAs may be used. A change of expression of one or more differentially expressed gene products (identified in Example 6) is used as an indicator of compound potency for induction of sciPS properties. Indicator cells are engineered from sciPS-MSCs by genetic modification such that induction or repression of a sciPS-MSC specific gene is detected by induction or repression of a fluorescent signal. For example, a reporter gene such as green fluorescent protein is fused to DNA encoding the regulatory elements of a sciPS specific gene and the construct is introduced into iPS-MSCs using standard recombinant DNA and transfection methods. Candidate agents that are selected as hits are subjected to a secondary screen to assess their effectiveness for inducing sciPS-MSC properties such as reduced rate of cellular aging and prolonged maintenance of differentiation capacity in treated iPS-MSCs.

Example 9: Repair of Wounds and Aging Skin Using Compounds Produced by sciPS Derived Cells MSCs are derived from sciPS cells and grown under standard culture conditions to 80% or greater confluence. The cells are washed with phosphate buffered saline and incubated in a defined serum free medium. The cell conditioned medium is collected following at least 16 hour incubation with cells. The conditioned medium is used directly or concentrated 5-10 fold by centrifugation through a low molecular weight cut-off filter (e.g. Amicon 3000MW cutoff). The conditioned medium is compared to identically prepared non-sciPS-MSC conditioned medium for wound healing properties and for ability to stimulate collagen production by human fibroblasts. Similarly, cell lysates are prepared from sciPS-MSCs and non-sciPS-MSCs and are tested for wound healing and collagen stimulating properties. Wound healing properties are tested using known in vitro and in vivo methods, n vitro methods include, without limitation, using the scratch assay and cell migration assay to assess the ability of the conditioned media and cell lysates to stimulate wound repair. Human dermal fibroblasts are incubated with conditioned medium or cell lysates from iPS-MSCs and sciPS-MSCs or equivalent control untreated medium for at least 16 hours and collagen content of the media tested using Sicrol Assay Kit (Biocolor Life Science Assays, United Kingdom).

All publications mentioned and/or referenced in the above specification are herein incorporated by reference. Various modifications and variations of the described methods will be apparent to those skilled in the art without departing from the scope and spirit of the invention. Although the invention has been described with respect to particular aspects or embodiments and/or further embodiments, it should be understood that the invention as claimed should not be unduly limited to such aspects and/or embodiments. It should also be understood that various modifications of the described modes for carrying out the invention, which would be readily known to and/or accessed through available information by those skilled in cellular studies or related fields, are intended to be within the scope of the following claims.

What is claimed is:

1. A method of generating stem cells having a reduced rate of cellular aging, the method comprising:
    a. collecting a cell sample from a validated supercentenarian individual, the cell sample comprising Epstein Barr Virus immortalized B-lymphoblastoid cells;
    b. reprogramming cells from the cell sample into induced pluripotent (iPS) cells, the reprogramming comprising integration-free episomal DNA comprising Oct4, Klf4, Sox2 and c-Myc;
    c. identifying supercentenarian induced pluripotent stem (sciPS) cells which exhibit telomere length resetting; and
    d. deriving stem cells which exhibit telomere length resetting from the sciPS cells, thereby generating stem cell having a reduced rate of cellular aging as compared to stem cells from iPS cells from a non-supercentenarian donor.

2. The method of claim 1, wherein the sciPS cells exhibit full telomere length resetting towards embryonic length.

3. The method of claim 1, wherein the supercentenarian individual is a human.

4. The method of claim 1, wherein the stem cells are mesenchymal stromal cells (MSC) or hematopoietic stem cells (HSC).

5. An isolated population of sciPS cells comprising iPS cells made by the method of claim 1.

6. The sciPS cells of claim 5, wherein the iPS cells exhibit telomere length resetting towards embryonic length.

7. The sciPS cells of claim 5, wherein the supercentenarian individual is a human.

8. An isolated population of stem cells derived from the sciPS cells of claim 5; wherein the stem cells exhibit telomere length resetting.

9. A method of identifying substances capable of tissue homeostasis and immune function regulation; the method comprising:
    a. culturing sciPS cells according to claim 5 and stem cells therefrom in growth media, and
    b. identifying substances in the growth media or in cell extracts.

10. A method of age-related disease relevant screening of candidate agent, the method comprising:
    a. contacting the candidate agent with a population of stem cells made by the method of claim 1; and
    d. determining the morphologic, genetic or functional effect of the candidate agent on the stem cells or on cells differentiated therefrom.

11. The method of claim 10, wherein the age-related disease is selected from the group consisting of osteoporosis, osteoarthritis, cancer, heart disease, stroke, and neurological disorders.

12. The method of claim 1, wherein the candidate agent is selected from the group consisting of biologics, small molecules, drugs, nutraceuticals, cosmeceuticals, compounds, and reagents.

13. The method of claim 10, wherein the stem cells are human stem cells.

14. The method of claim 10, wherein the stem cells exhibit full telomere length resetting towards embryonic length.

15. The method of claim 10, wherein the stem cells are MSCs or HSCs.

16. A method of screening candidate agents for the ability to confer properties of stem cells made by the method of claim 1, the method comprising:
    a. contacting the candidate agent with a population of non-sciPS cells;
    b. comparing the cells resulting from step a with stem cells made by the method of claim 1; and
    c. identifying agents which are capable of conferring properties of stem cells made by the method of claim 1 to the non-sciPS cells.

17. The method of claim 16, wherein the candidate agent is selected from the group consisting of biologics, small molecules, drugs, nutraceuticals, cosmeceuticals, compounds, and reagents.

18. The method of claim 16, wherein the properties of stem cells made by the method of claim 1 conferred to the non-sciPS cells are a reduced rate of cellular aging as compared to non-sciPS cells without the candidate agent.

19. The method of claim 16, wherein the non-sciPS cells are human.

* * * * *